United States Patent
Wilcox et al.

(10) Patent No.: US 7,499,772 B2
(45) Date of Patent: Mar. 3, 2009

(54) METHOD AND SYSTEM FOR NAVIGATING A NONDESTRUCTIVE EVALUATION DEVICE

(75) Inventors: David E. Wilcox, Gilbert, AZ (US); Paul Michael Jones, Glendale, AZ (US); Timothy R. Duffy, Chandler, AZ (US)

(73) Assignee: Honeywell International Inc., Morristown, NJ (US)

( * ) Notice: Subject to any disclaimer, the term of this patent is extended or adjusted under 35 U.S.C. 154(b) by 423 days.

(21) Appl. No.: 11/217,268

(22) Filed: Aug. 31, 2005

(65) Prior Publication Data

US 2007/0113690 A1   May 24, 2007

(51) Int. Cl.
*G01M 7/00* (2006.01)
(52) U.S. Cl. .................. 701/3; 73/865.8; 73/865.9; 702/36; 703/8
(58) Field of Classification Search ..... 73/865.8–865.9, 73/866.5; 701/3; 702/33–40, 113; 703/8
See application file for complete search history.

(56) References Cited

U.S. PATENT DOCUMENTS

| | | | |
|---|---|---|---|
| 3,739,176 A | 6/1973 | Thorn | |
| 3,751,169 A | 8/1973 | Fornerod | |
| 4,453,085 A | 6/1984 | Pryor | |
| 4,602,163 A | 7/1986 | Pryor | |
| 5,077,671 A * | 12/1991 | Leslie et al. ............... | 701/3 |
| 5,100,229 A | 3/1992 | Lundberg et al. | |
| 5,359,542 A | 10/1994 | Pahmeier et al. | |
| 5,374,830 A | 12/1994 | Pryor | |
| 5,461,473 A | 10/1995 | Pratt et al. | |
| 5,666,202 A | 9/1997 | Kyrazis | |
| 5,742,069 A | 4/1998 | Steenwyk et al. | |
| 5,777,891 A * | 7/1998 | Pagano et al. ............... | 702/39 |
| 6,324,296 B1 | 11/2001 | McSheery et al. | |
| 6,653,650 B2 | 11/2003 | McMillan et al. | |
| 6,727,511 B2 | 4/2004 | Cusick et al. | |
| 6,762,847 B2 | 7/2004 | Duquette et al. | |
| 6,904,380 B1 * | 6/2005 | Brayton et al. ............... | 702/108 |
| 7,267,020 B2 * | 9/2007 | Wilcox et al. ............... | 73/866.5 |
| 2002/0038855 A1 | 4/2002 | Hwang | |
| 2002/0100884 A1 | 8/2002 | Maddock | |

(Continued)

FOREIGN PATENT DOCUMENTS

DE        2701823 A1      8/1977

OTHER PUBLICATIONS

EP Search Report, 06125682.2 dated Jul. 4, 2007.

*Primary Examiner*—Thomas P Noland
(74) *Attorney, Agent, or Firm*—Fogg & Powers LLC

(57) ABSTRACT

A system for the nondestructive evaluation of aircraft comprising a plurality of positional transmitters forming a perimeter around a test airplane and an inspection station within the perimeter. The inspection station includes a moveable cart, a nondestructive testing device coupled the cart, and a computer coupled to the cart and nondestructive testing device. The computer configured to receive aircraft positional data from positional receivers mounted on an aircraft and overlay a model of the aircraft on the received aircraft positional data to determine a coordinate system for the aircraft. The computer is further operable to determine the location of the cart from data received from onboard positional receivers, the location of the cart referenced to the coordinate system for the aircraft.

16 Claims, 13 Drawing Sheets

U.S. PATENT DOCUMENTS

| | | |
|---|---|---|
| 2002/0179866 A1 | 12/2002 | Hoeller et al. |
| 2003/0043964 A1 | 3/2003 | Sorenson |
| 2003/0089183 A1 | 5/2003 | Jacobsen et al. |
| 2007/0078618 A1* | 4/2007 | Wilcox et al. ............... 702/113 |

* cited by examiner

METHOD AND SYSTEM FOR NAVIGATING A NONDESTRUCTIVE EVALUATION DEVICE

TECHNICAL FIELD OF THE INVENTION

This invention relates to the field of structural testing and, more specifically, to a method and system for navigating a nondestructive evaluation device.

BACKGROUND OF THE INVENTION

The periodic, nondestructive testing of large structures, such as passenger vehicles, is important to assist in the evaluation of structural integrity. For example, aircraft undergo nondestructive testing in order to detect structural variations or changes such as structural fatigue. An example of a aircraft component that is periodically inspected for structural changes or variations is the outer surface of the fuselage. However, the size of the fuselage makes nondestructive testing a difficult undertaking.

One approach used for nondestructive testing of an aircraft fuselage and other large structures involves a trained operator performing tests with portable equipment. This approach has a number of drawbacks including that it is a slow process and requires a specially trained individual. Another approach used for the nondestructive testing of large structures utilizes a robotic vehicle. The robotic vehicle automatically maneuvers itself to the test subject and performs nondestructive testing at various points on the test subject. However, this degree of automation results in high costs and complex systems. Additionally, the proper mounting and alignment of testing devices is difficult.

In view of the foregoing, it is desirable to provide a method for navigating a nondestructive evaluation device that addresses one or more of the foregoing deficiencies or other deficiencies not implicitly or expressly described. It is also desirable to provide an apparatus for navigating a nondestructive evaluation device that addresses one or more of the foregoing deficiencies or other deficiencies not implicitly or expressly described. Furthermore, other desirable factors and characteristics of the present invention will become apparent from the subsequent detailed description and the appended claims, taken in conjunction with the accompanying drawings and the foregoing technical field and background.

SUMMARY OF THE INVENTION

In one embodiment of the invention, an inspection device for nondestructive evaluation of an aircraft comprises a cart; a nondestructive testing device coupled the cart; and a computer coupled to the cart and nondestructive testing device. The computer is configured to receive aircraft positional data from positional receivers mounted on an aircraft and then to overlay a model of the aircraft on the received aircraft positional data to determine a coordinate system for the aircraft. The computer is further configured to determine the location of the cart from data received from onboard positional receivers, the location of the cart referenced to the coordinate system for the aircraft.

A system for the nondestructive evaluation of aircraft comprising a plurality of positional transmitters forming a perimeter around a test airplane and an inspection station within the perimeter. The inspection station includes a moveable cart, a nondestructive testing device coupled the cart, and a computer coupled to the cart and nondestructive testing device. The computer configured to receive aircraft positional data from positional receivers mounted on an aircraft and overlay a model of the aircraft on the received aircraft positional data to determine a coordinate system for the aircraft. The computer is further operable to determine the location of the cart from data received from onboard positional receivers, the location of the cart referenced to the coordinate system for the aircraft.

In another embodiment, A method for nondestructive evaluation of an aircraft using an inspection cart having a nondestructive testing device comprises receiving aircraft positional data from positional receivers mounted on the aircraft. Next, a model of the aircraft overlaid on to the received aircraft positional data to determine a coordinate system for the aircraft. Then the location of the inspection cart can be determined from data received from onboard positional receivers. The location of the inspection cart is referenced to the coordinate system for the aircraft.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures:

DETAILED DESCRIPTION OF THE DRAWINGS

The following detailed description is merely illustrative in nature and is not intended to limit the invention or the application and uses of the invention. Furthermore, there is no intention to be bound by any expressed or implied theory presented in the preceding technical field, background, brief summary or the following detailed description.

Figure 1:
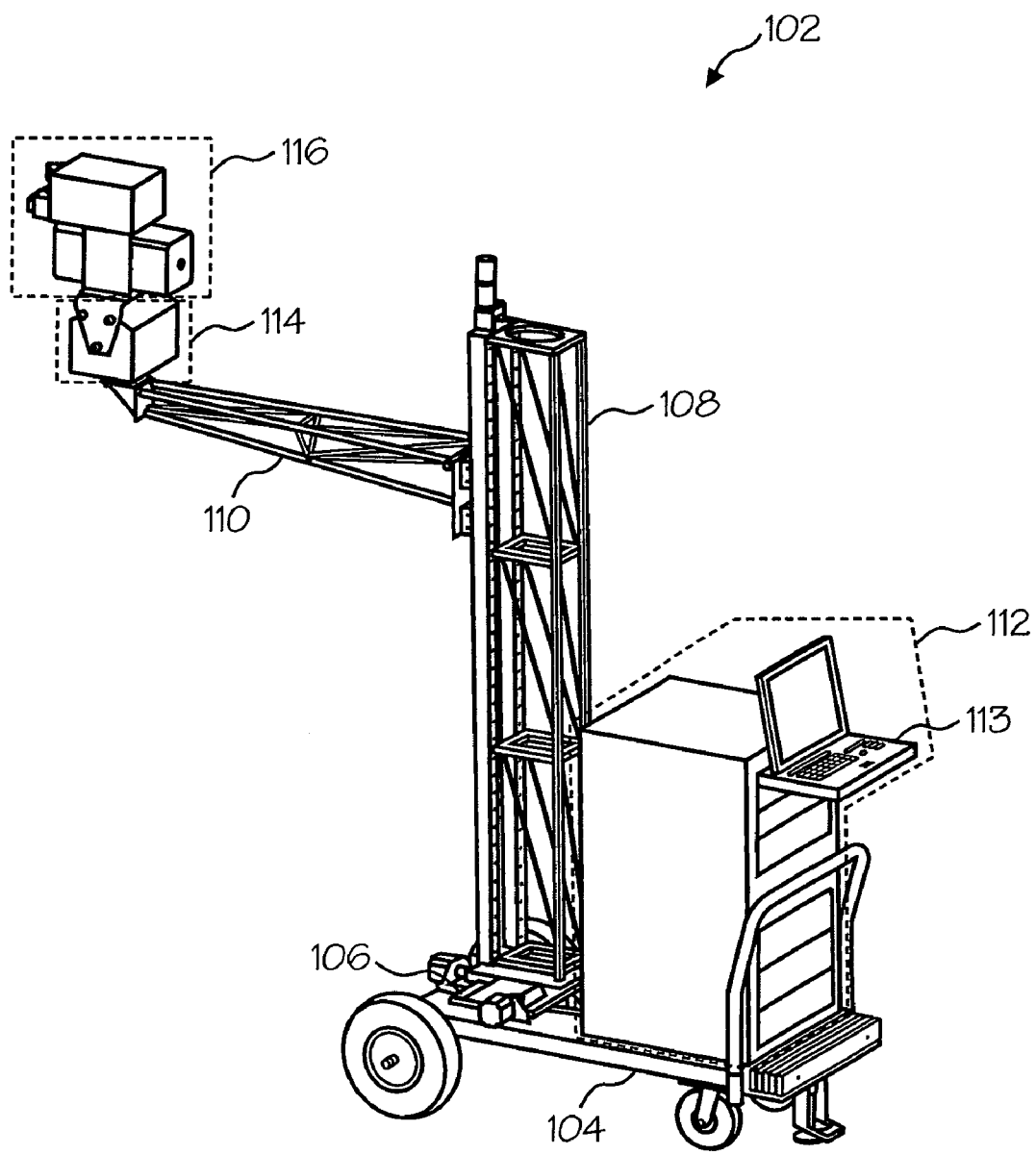
FIG. 1 illustrates an inspection station in accordance with an exemplary embodiment of the present invention.
Figure 2:
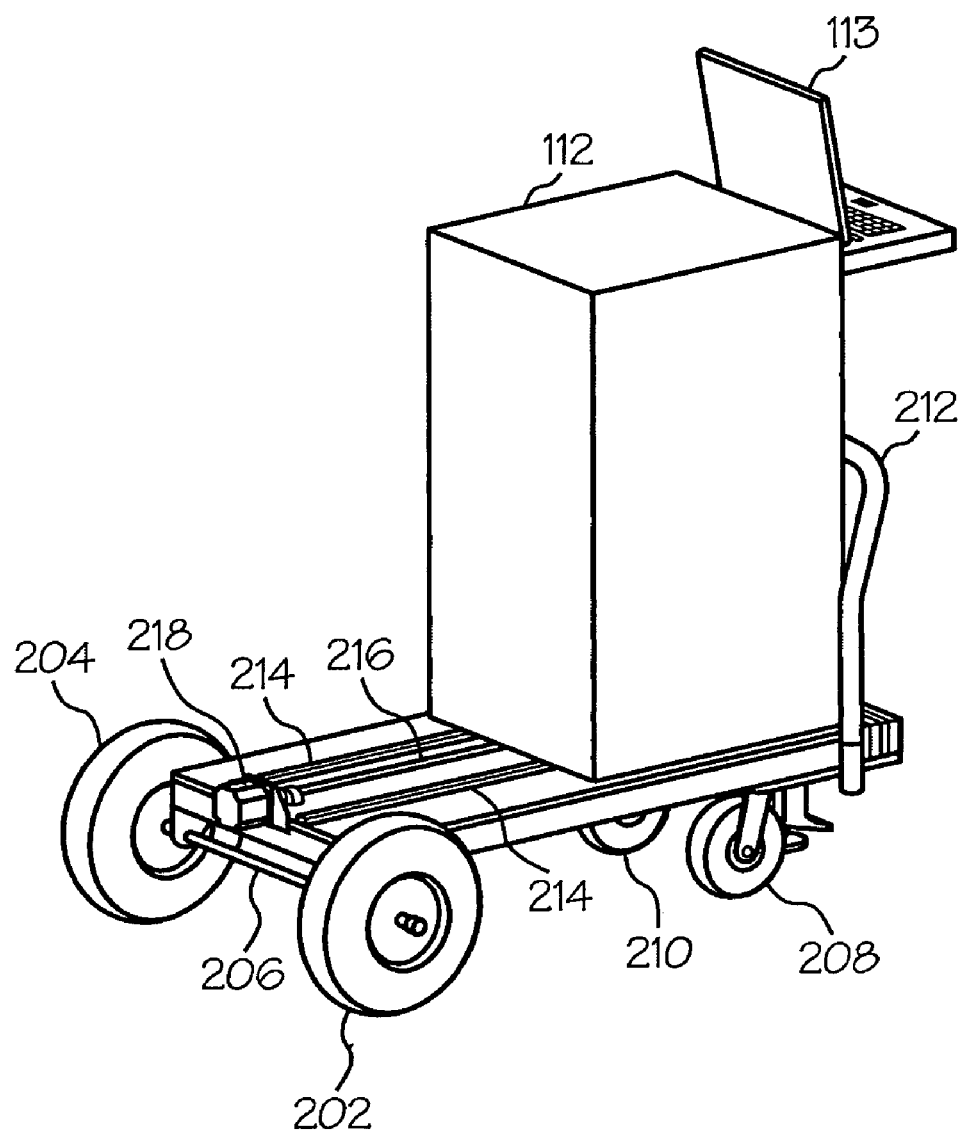
FIG. 2 illustrates a cart in accordance with an exemplary embodiment of the present invention.

FIG. 1 illustrates an exemplary embodiment of the present invention. As seen in FIG. 1, an inspection station 102 comprises a cart 104, a sliding table 106, a vertical tower 108, a boom 110, an electronic rack 112, a pan-tilt head 114, and nondestructive test device 116. Cart 104 allows the inspection station 102 to move from one location to another. As seen in FIG. 2, cart 104 includes two front wheels 202 and 204 coupled by a front axis 206 and two rear wheels 208 and 210. In one exemplary embodiment, one or more of the wheels can swivel to allow for movement of the cart 104. A handle section 212 provides an area for the operator to grasp when maneuvering the inspection station. The electronic rack 112 can be mounted on the cart section 104.

The electronic rack 112 can include controls for operating the nondestructive test device and the moving components of the inspection station 102. The electronic rack 112 can also include a computer 113, such as a laptop computer, that is operable to provide automatic control of the nondestructive testing operation, as well as to collect generated data. For example, the computer 113 can control the movement of various motors and other equipment to adjust the positioning of the nondestructive test device 116. The computer 113 can also provide information as to the relative location of the inspection station 102.

Figure 3:
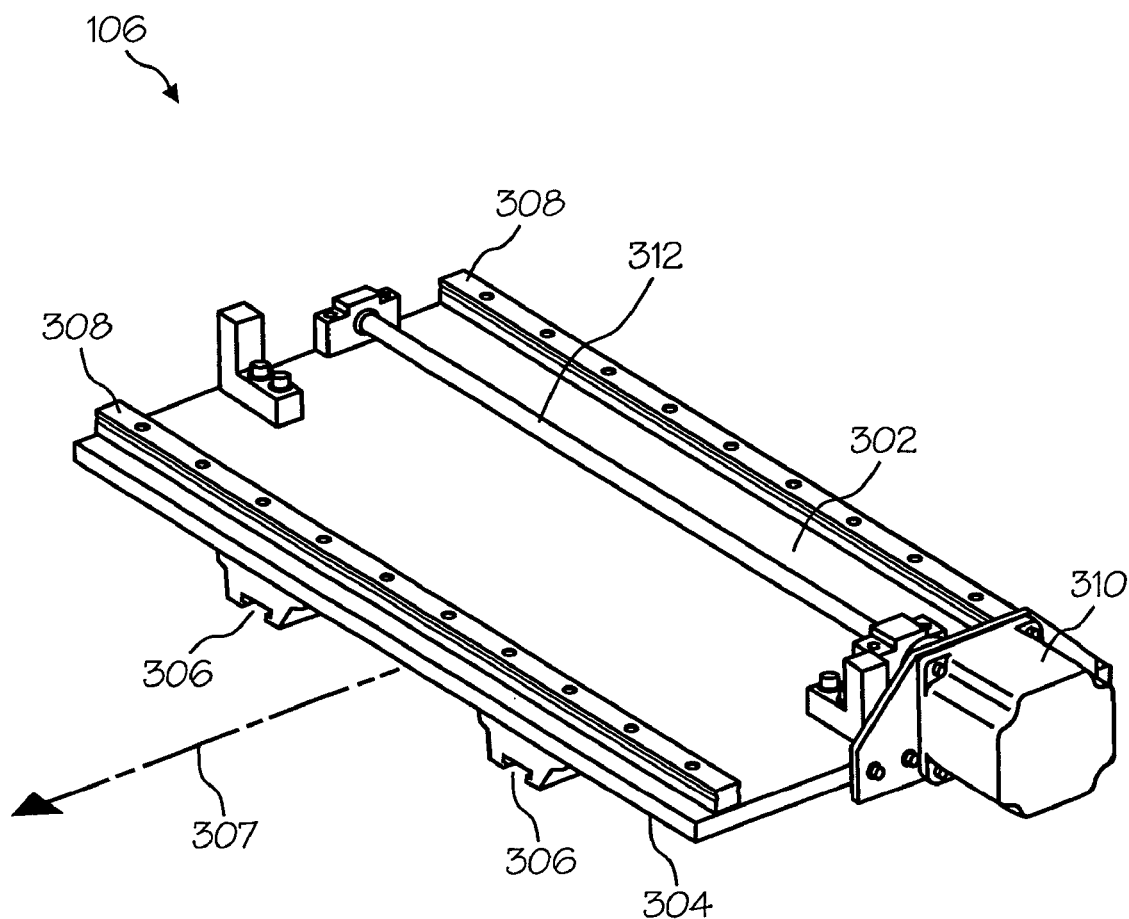
FIG. 3 illustrates a sliding table in accordance with an exemplary embodiment of the present invention.

Sliding table 106, illustrated in detail in FIG. 3, provides two degrees of freedom for the inspection station 102. The sliding table 106 allows for movement of the vertical tower 108 (and therefore, the components connected to the vertical tower 108) in two directions; one direction along an imaginary line 307 bisecting the axis of the front wheels and another direction perpendicular to the first direction. In an exemplary embodiment, sliding table 106 has a top side 302 and a bottom side 304. Bottom side 304 includes a pair of x-axis bearings 306, and an x-axis nut drive (not shown). The top side 302 includes y-linear guides 308, a y-drive motor 310, and a y-lead screw 312.

Figure 4:
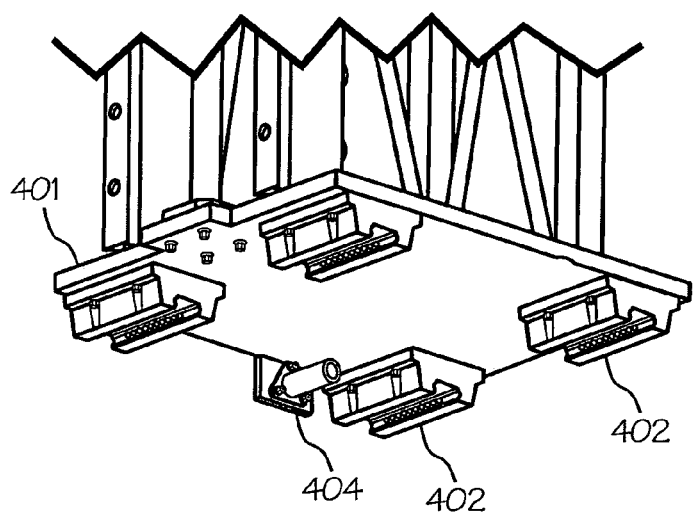
FIG. 4 illustrates a base of a vertical tower in accordance with an exemplary embodiment of the present invention.

Referring to FIGS. 2 and 3, X-axis bearings 306 engage x-linear guides 214 mounted on to cart section 104 to allow sliding table 106 to move in a direction along the line 307. The x-axis drive nut (not shown) couples to an x-axis lead screw 216 to allow for movement along the x-linear guide using, in an exemplary embodiment, a stepper motor 218. Other methods of moving the sliding table 106 are available. Y-linear guides 308 engage y-bearings 402 mounted on the base 401 of the vertical tower 108 for movement of the vertical tower 108 perpendicular to the x-axis movement as shown in FIG. 4. The y-lead screw 312 that is powered by the y-drive motor 310 couples to the y-drive nut 404 to move the vertical tower 108. The sliding table 106, in one exemplary embodiment, provides movement to adjust the nondestructive test device 116 when the inspection station 102 is near the test subject, as will be discussed in detail below. In one exemplary embodiment, sliding table 106 can move approximately 5 inches forward along the line 307 and the vertical tower 108 can move approximately five inches back and forth along the y-linear guides 308.

Figure 5:
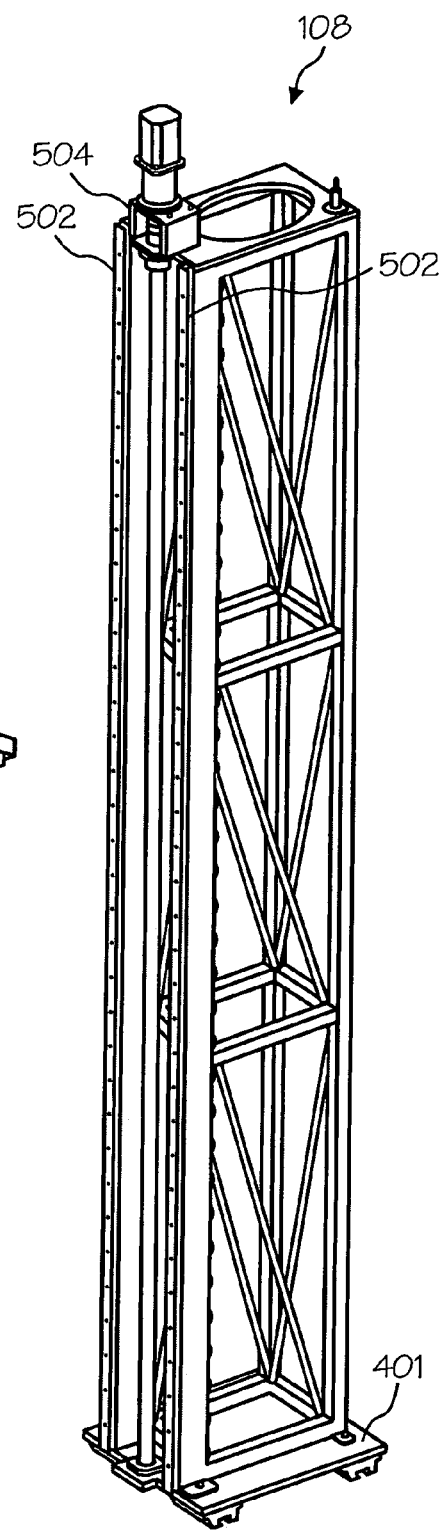
FIG. 5 illustrates a vertical tower in accordance with an exemplary embodiment of the present invention.

Vertical tower 108 supports boom 110 and allows for the boom 110 to move up and down to adjust the position of the nondestructive test device 116, thereby providing one degree of freedom to the inspection station 104. As seen in FIG. 5, vertical tower 108 has two vertically mounted rails 502 upon which the boom 110 can travel. In one exemplary embodiment, vertical tower 108 also includes a drive system 504 for powering the movement of the boom 110, although other methods of moving the boom 110 can also be used. Vertical tower 108 can be sized to match the size of the test subject and can include multiple vertical sections.

Figure 6:
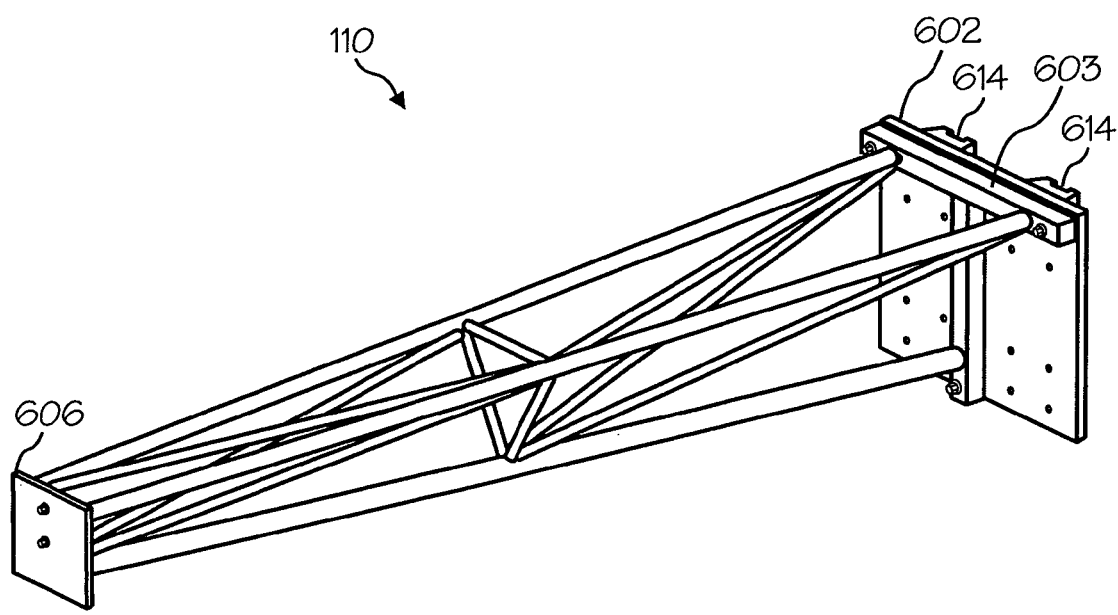
FIG. 6 illustrates a boom in accordance with an exemplary embodiment of the present invention.

Turning to FIG. 6, boom 110 couples to the vertical tower 108 at a first end 602 of the vertical tower 108 such that the boom 110 is essentially perpendicular to and extends out from the vertical tower 108. Boom 110 provides support for the pan-tilt head 114. In one exemplary embodiment, the first end 602 includes a bottom 603 having bearings 614 that allow for movement up and down the two vertically mounted rails 502 of vertical tower 108. Boom 110 also includes a mounting surface 606 upon which the pan-tilt head 114 can be attached.

Figure 7:
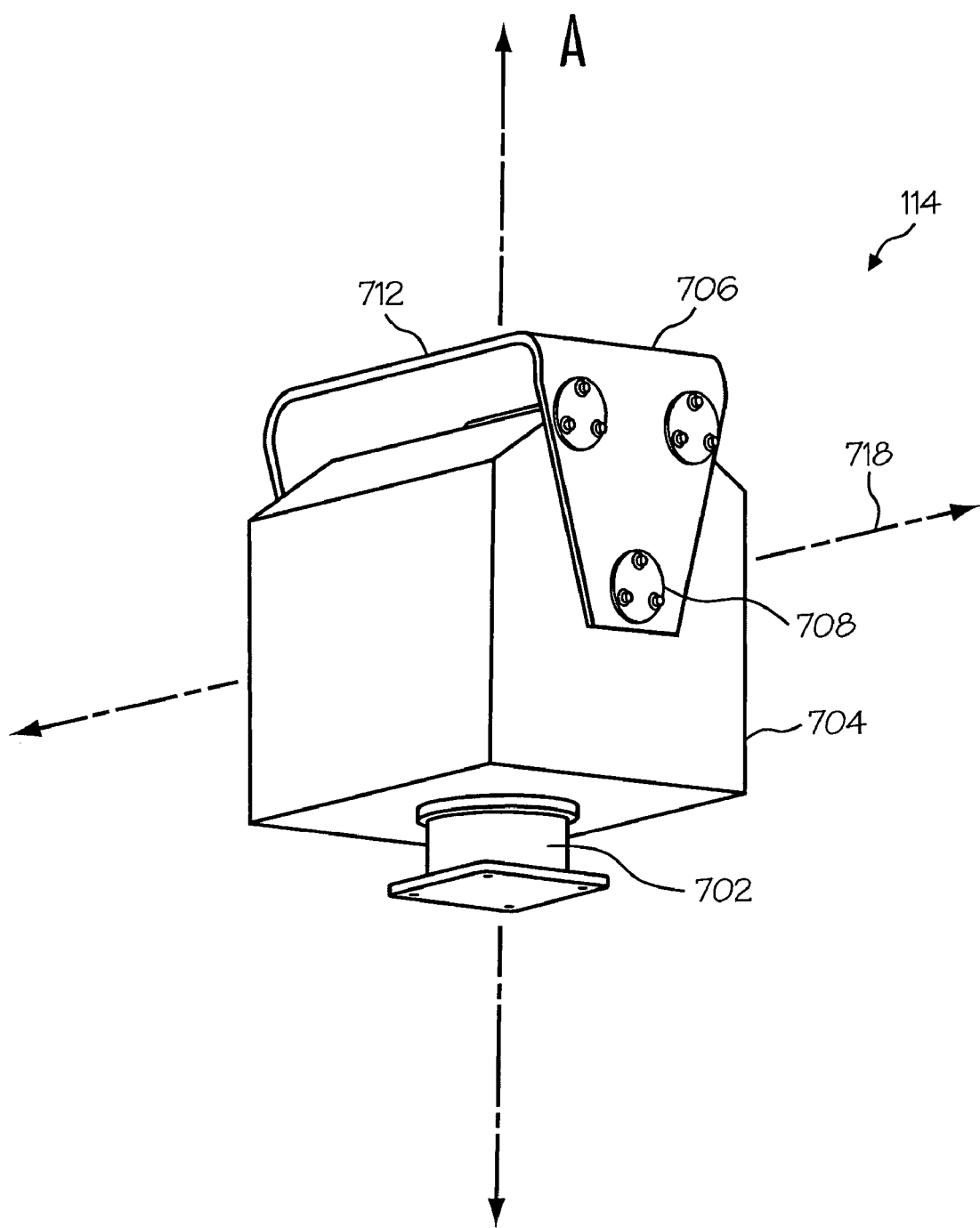
FIG. 7 illustrates a pan-tilt adjuster in accordance with an exemplary embodiment of the present invention.

Turning to FIG. 7, pan-tilt head 114 couples to the mounting surface 606 of the boom 110 and provides two degrees of freedom. In an exemplary embodiment, pan-tilt head 114 includes a pan bearing 702 that couples at one end of to the mounting surface 606 and the other end to a pan body 704. A tilt bracket 706 couples at a first portion 708 to the pan body 704. The pan bearing 702 allows the pan body 704 to rotate about axis A. The tilt bracket 706 includes a mounting surface 712 for mounting nondestructive test device 116. Mounting surface 712 preferably pivots about tilt axis 718.

Figure 8:
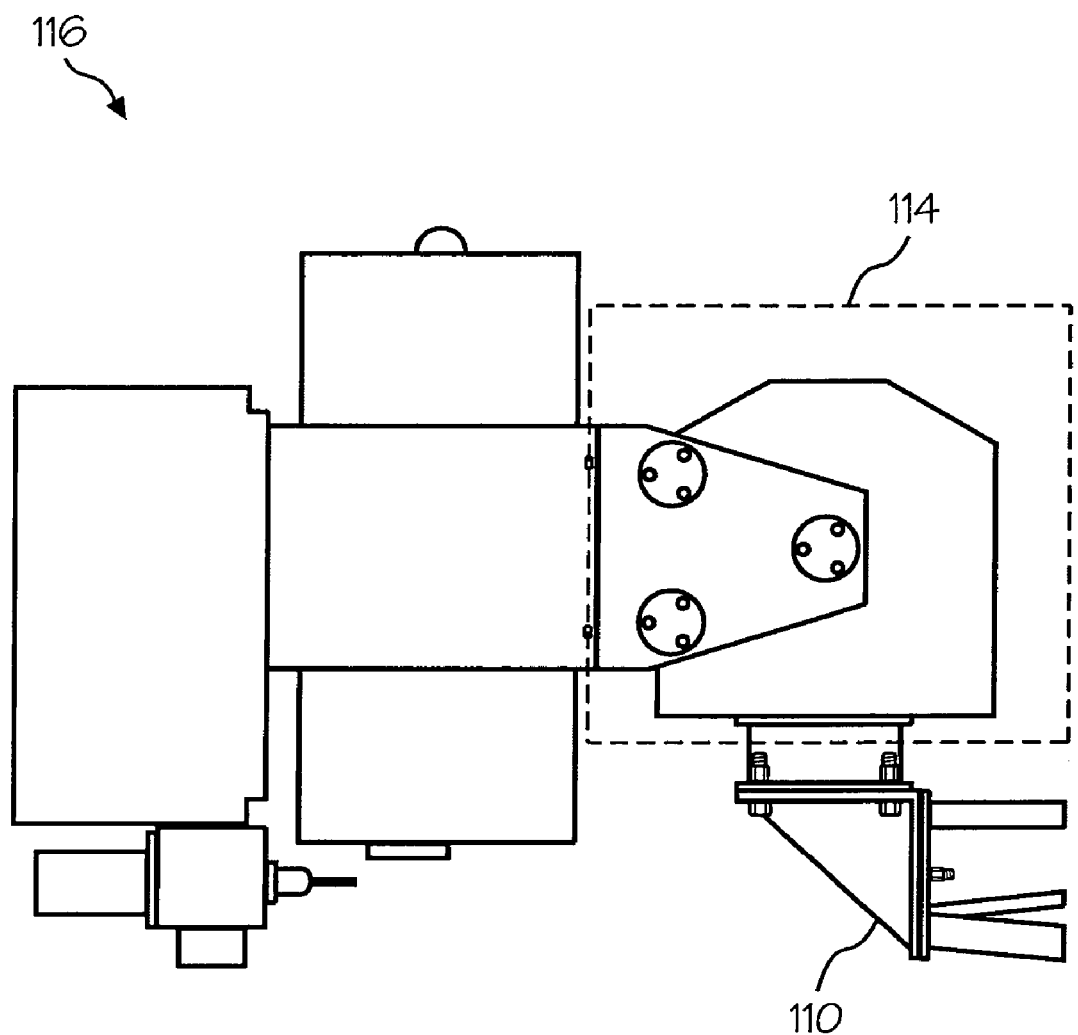
FIG. 8 illustrates a nondestructive testing package in accordance with an exemplary embodiment of the present invention.

In FIG. 8, the nondestructive test device 116 is coupled to pan-tilt head 114. The nondestructive test device 116 can be any one of a number of testing devices such as an inspection camera for visual inspection of a surface, a vibrometer for performing vibration analysis testing, an eddy current tester, an ultrasonic tester, and the like. However other nondestructive testing devices can be used in accordance with the present invention. In one embodiment, the nondestructive test device 116 can perform other maintenance functions. For example, the nondestructive test device can be a painting device for painting the test structure, a cleaning device for cleaning the test subject, a de-icing device for removing ice from the test subject, or any other tool that requires the device to be moved to different areas of the aircraft.

In an exemplary embodiment of the present invention, a user maneuvers the inspection station 102 proximate to where the testing will take place. For example, the user can maneuver the inspection station 102 up to an aircraft and stop at a predetermined location. The inspection station 102 can then, either through manual control or automatic control, be maneuvered to place the nondestructive test device 116 to the proper location and alignment to use the nondestructive test device and the nondestructive test. In the exemplary embodiment, where the nondestructive test device 116 is manually maneuvered to a test position, the user can determine the place to position the nondestructive test device 116 based on either what the users can see directly or through the use of a visual guide such as a camera.

Figure 9:
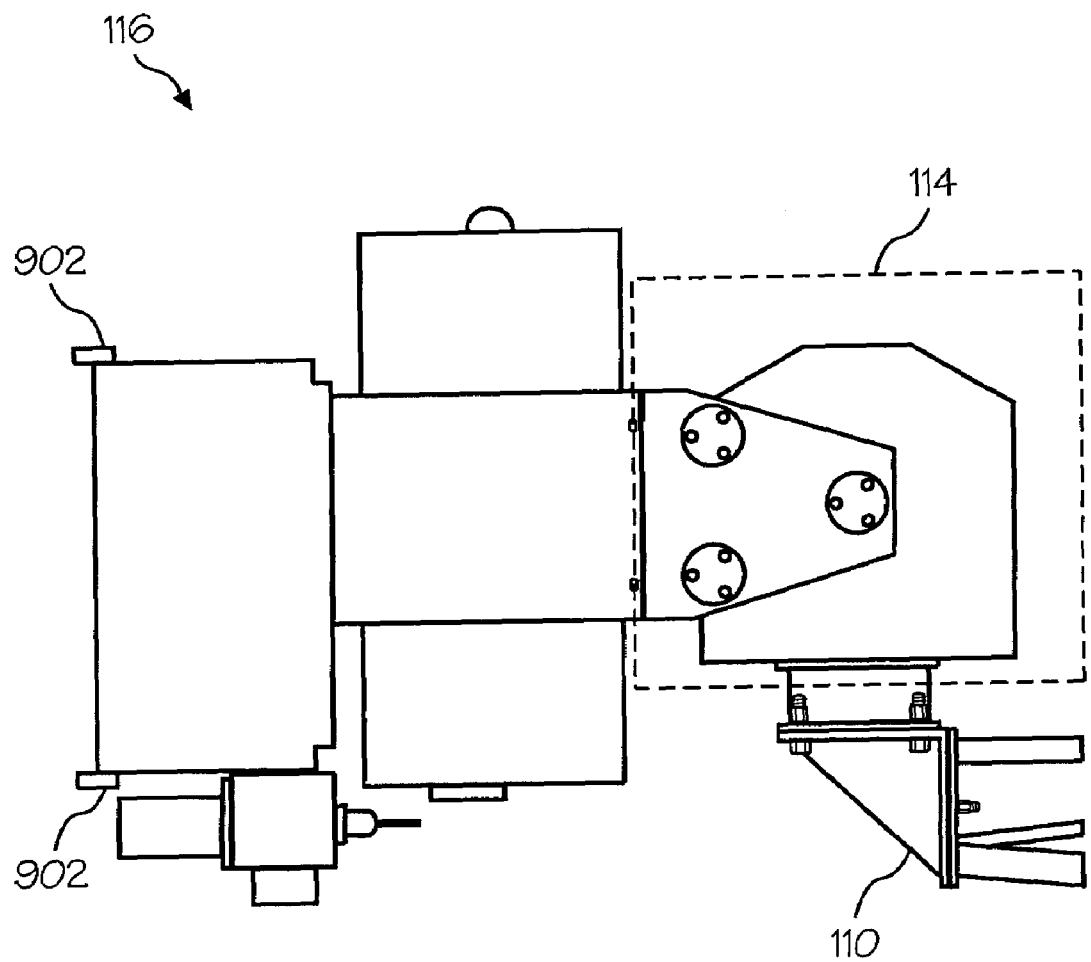
FIG. 9 illustrates an use of the inspection station in accordance with an exemplary embodiment of the present invention.

FIG. 9 illustrates the nondestructive test device 116 with the addition of distance sensors 902. Distance sensors 902 indicate how far the sensors are from a target, such as the test subject. By mounting the distance sensors 902 on the nondestructive test device 116, the distance sensors 902 can provide feedback as to the distance between nondestructive test device 116 and the test subject. This information can be used to assist an operator in positioning the inspection station 102. Once in a desired position, the distance sensors 902 can provide data to the computer 113 in order to move the vertical tower 108, the boom 110, and pan-tilt head 114 to set the nondestructive test device 116 to the proper distance for testing. The distance sensors 902 can be ultrasonic distance sensors, optical distance sensors, laser distance sensors, and the like. By first manually positioning the inspection station 102 and then aligning the nondestructive test device 116, the potential is reduced for striking the test subject with the inspection station. Alternatively, the distance sensors 902 can provide feedback to the operator in order to manually position the test device.

Additionally, pressure sensors can be used to provide information as to how much force is contacting the test subject in situation where the nondestructive testing device touches the surface of the test subject. For example, ultrasonic testers typically require contact with the test subject.

Figure 10:
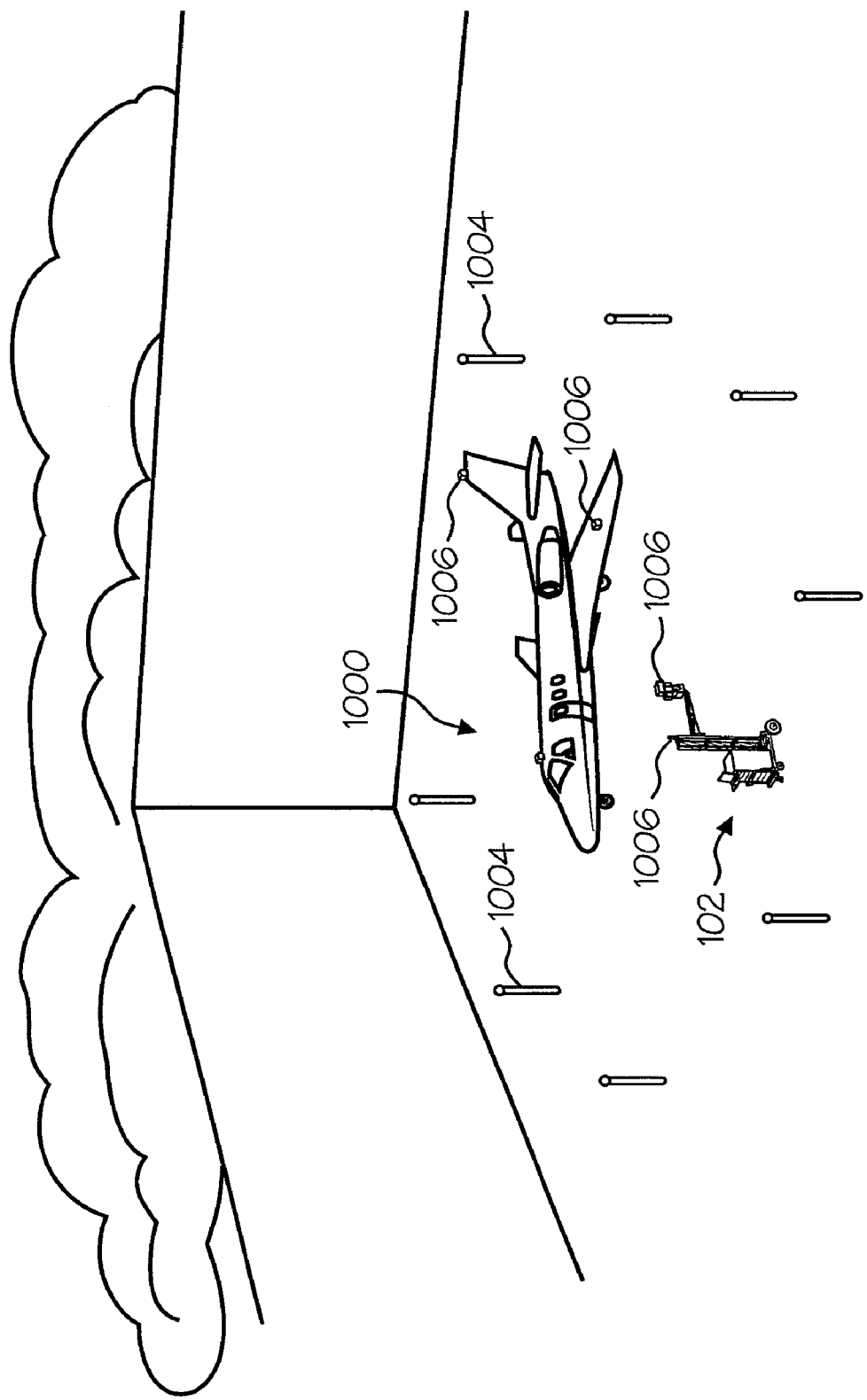
FIG. 10 illustrates an exemplary localized positioning system and an inspection station in accordance with an exemplary embodiment of the present invention.

In another embodiment, a localized positioning system is employed to determine the positioning of the inspection station 102. FIG. 10 illustrates an exemplary embodiment of a localized positioning system 1000. Inside of a hanger 1001 or similar large structure are an aircraft 1002 and the inspection station 102. At least two transmitters 1004 are placed in fixed locations in the hanger 1001. Receivers 1006 are placed on the aircraft 1002 and the inspection station 102. Transmitter 1004, in an exemplary embodiment, sends signals to the receivers 1006, which the receivers 1006 can use to determine the azimuth (horizontal angle) and the elevation (vertical angle) from the transmitter 1004 to the receiver 1006. By receiving the azimuth and elevation information from at least two transmitters 1004, the receiver 1006 can determine its position.

In one exemplary embodiment, the transmitters 1004 are first calibrated and then installed. During the installation process the placement and orientation of each transmitter 1004 can be determined. Optionally, the transmitters 1004 may be fixed, which allows for the transmitters 1004 in the system to monitor each other for any degradation in performance. Both the receivers 1006 and the transmitters 1004 can send information to the computer 113 or other computer devices to provide navigational and positional information. The connection between the computer 113 and the transmitters 1004 and the receivers 1006 are preferably wireless, although a wired connection can be used.

In one exemplary embodiment, each transmitter generates three signals: two infrared laser beams which fan outwards and rotate in the rotating head of the transmitter 1004, and a LED strobe light. As discussed previously, the receiver 1006 can determine the azimuth and elevation values between the transmitter 1004 and the receiver 1006. Once two or more transmitters 1004 signals are received by one of the receivers 1006, the receiver 1006 can determine its position. Receiver 1006 can be placed on any object to determine the objects location. As an object with a receiver 1006 moves through an area where there are transmitters 1004, the location of the object can be updated.

In one embodiment, the localized position system 1001 can be used to assist the operator in positioning the cart 104 as well as assisting in the placement of the nondestructive test device 116. Instead of distance detectors such as ultrasonic distance detectors, the localized positioning system can be used. In another exemplary embodiment, the location of a test object, as determined by the localized positioning system 1001, can be used in conjunction with a predetermined electronic model of the object to assist in the maneuvering of the cart 104 and the positioning of nondestructive test device 116.

Figure 11:
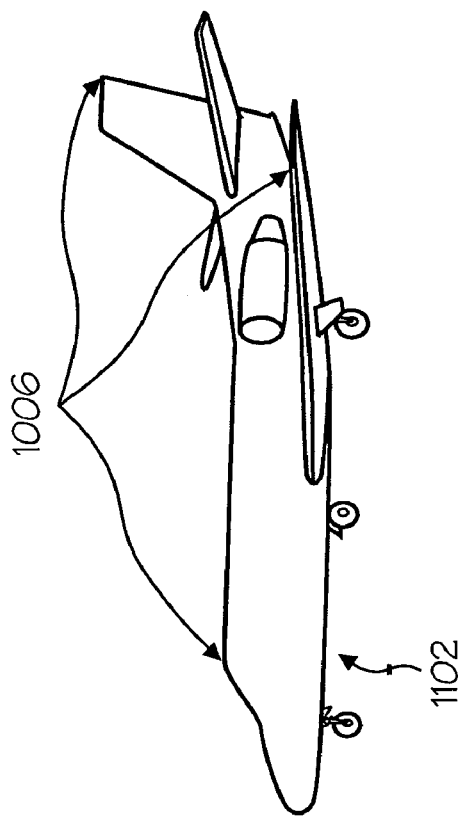
FIG. 11 illustrates an aircraft with positioned receivers in accordance with an exemplary embodiment of the present invention.
Figure 11:
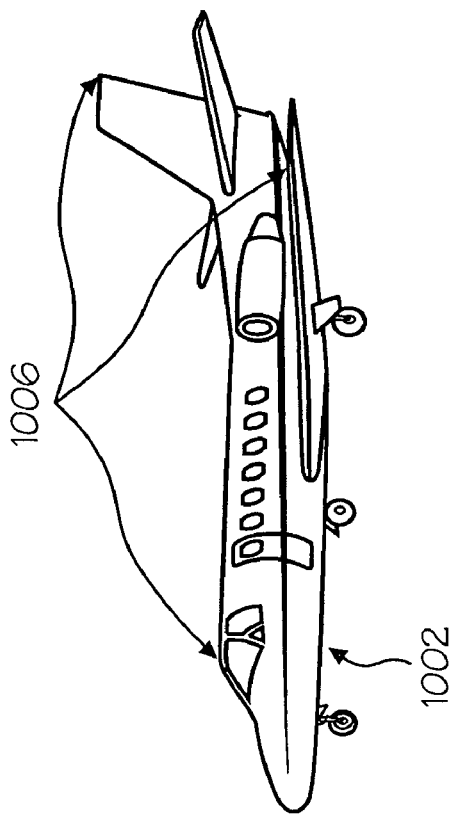

For example, FIG. 11 illustrates the aircraft 1002 upon which three receivers 1006 have been installed and a three dimensional model 1102 of the aircraft. The positions of the three receivers 1006 are determined as discussed previously. The location of the three receivers 1006 can then be compared to a three dimensional model 1102 of the aircraft stored in computer 113 to generate a three dimensional representation of the aircraft. Various different aircraft models 1102 can be stored in the memory of the computer 113. Then, when a particular type of aircraft is being inspected, a model of that aircraft can be retrieved from memory. Models of different aircraft can be obtained from the manufacturer of the aircraft or generated from design schematics of the aircraft. Once a model aircraft is selected, a best square fit or other technique can be used to fit the selected model on to the data points of the aircraft.

Figure 12:
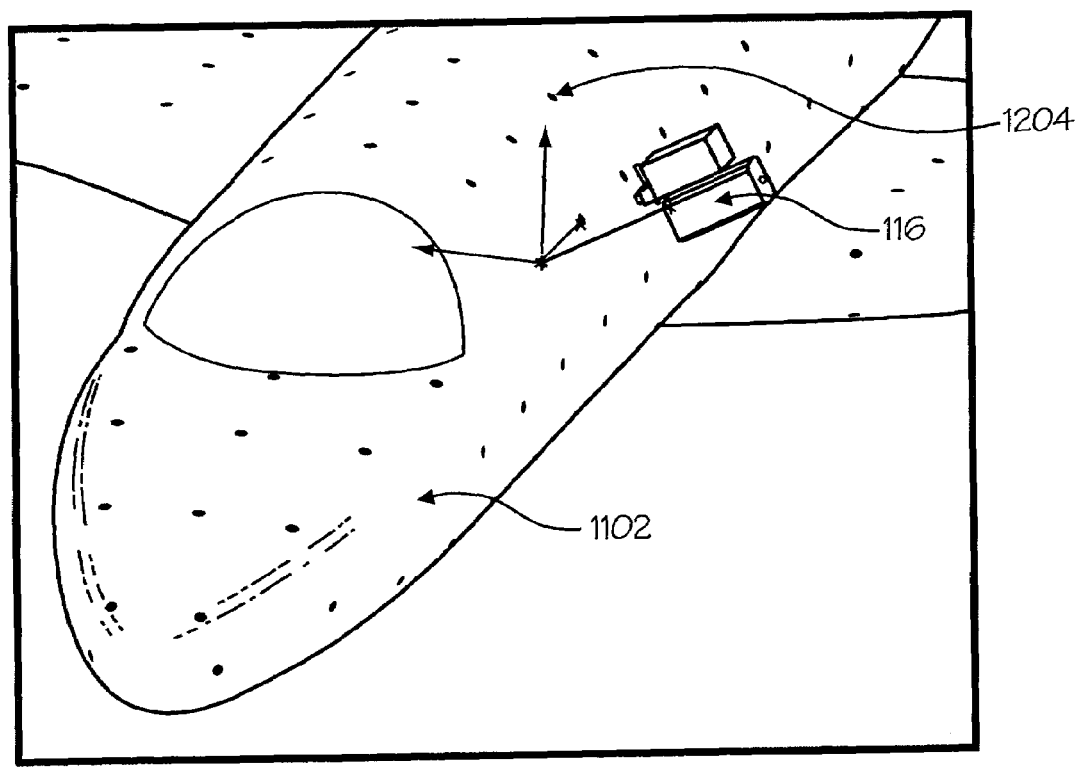
FIG. 12 illustrates a model aircraft with testing points in accordance with an exemplary embodiment of the present invention.

The ability to overlay a model aircraft body over an aircraft allows for individual testing locations on the plane to be determined and referred to using a plane specific reference coordinate system. For, example, FIG. 12 illustrates the aircraft model 1102 having a number of predetermined testing points 1204 that can be included as part of the model aircraft data. Also, various test procedures use the testing devices that are offset a certain distance from the aircraft. Since each testing point 202 can be located in a coordinate system, a test vector can be generated for each testing point 1204 that indicates where the nondestructive test device 116 should be positioned. Therefore, once a computer model of the aircraft is generated any point along the aircraft can be located using the coordinate system that is used to locate the aircraft's position. By selecting a testing point 1204, the operator of the cart 104 can manually move the cart to a position near the test point 1204 and then the nondestructive test device 116 can finish its final positioning automatically, as described previously.

Figure 13:
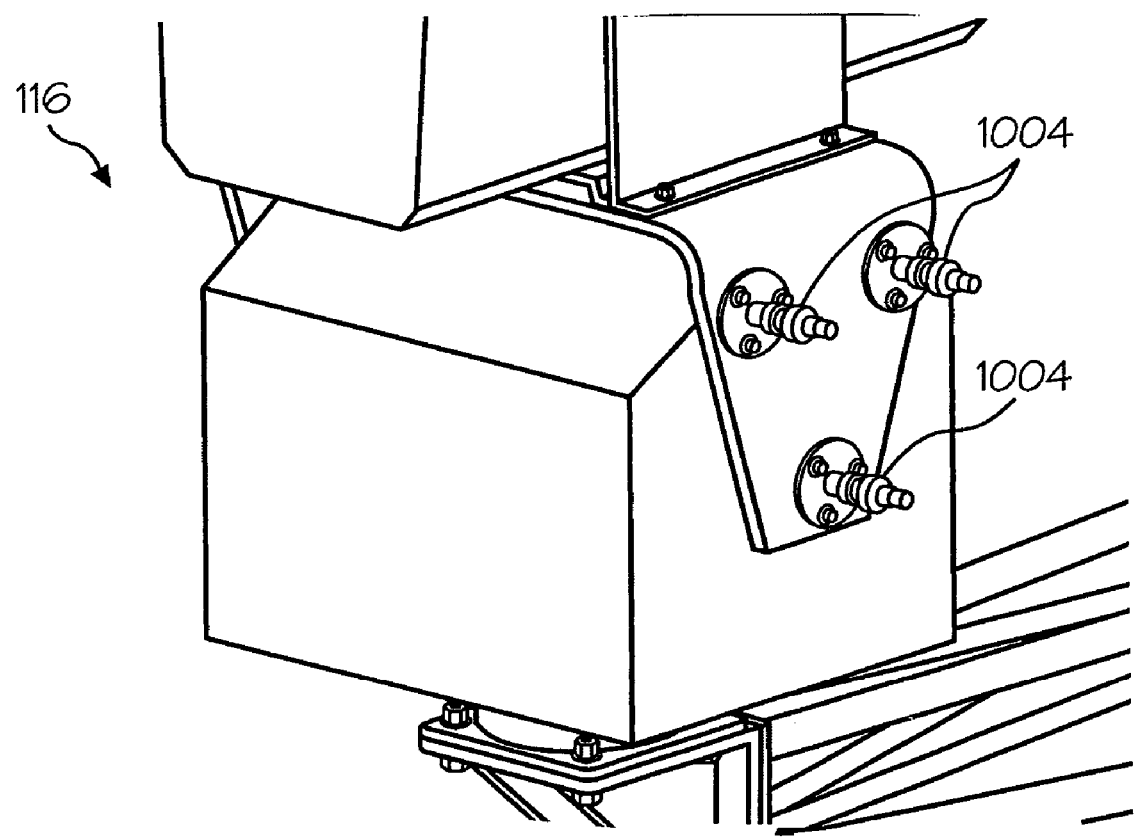
FIG. 13 illustrates positional receivers mounted on an inspection station in accordance with an exemplary embodiment of the present invention.

In addition to determining the position of the test subject, the position of the inspection station 102 can also be detected. As illustrated in FIG. 13, three receivers 1006 can be placed on the nondestructive test device 116. This will allow three dimensional tracking of the nondestructive test device 116. A fourth receiver 1006 can be placed at the top of the vertical tower 108 to provide information regarding the annular relationship between the nondestructive test device 116 and the cart 104. A mapping can also be made to produce a computer representation, or model form, of the inspection station 102 that can be used in conjunction with the three dimensional model of the test aircraft mapping. Thus, the nondestructive test device's 116 location is mapped into the same coordinate system as the aircraft.

Figure 14:
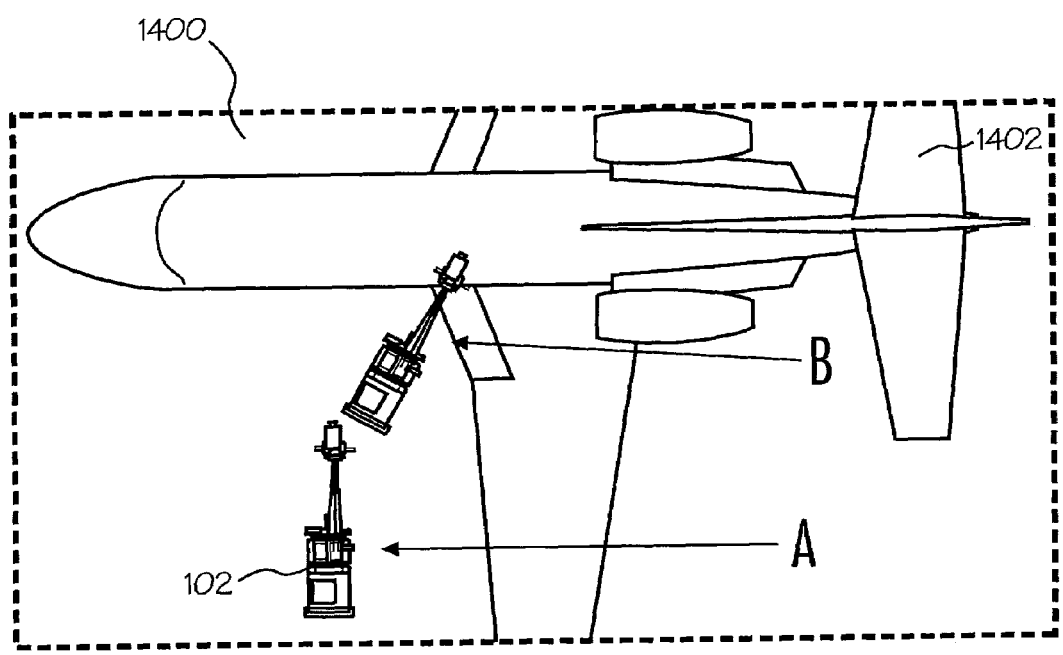
FIG. 14 illustrates a computer image of an inspection station and a test vehicle in accordance with an exemplary embodiment of the present invention.

FIG. 14 illustrates a computer image 1400 showing the test vehicle 1402, and the inspection station at a first position "A." In an exemplary embodiment, the computer image 1400 is displayed on computer 113. In the exemplary embodiment, the operator can either enter the coordinates of a test location, or visually locate the testing area. Then the operator will move the cart 104 towards the testing area. Once the cart 104 is in range, feedback, such as the sounding of an alarm or a computer image of the cart in the proper location, as seen as the inspection station at position "B," can be provided. Once in the proper location, the nondestructive testing device 116 can automatically position itself as discussed previously.

The example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention as set forth in the appended claims and the legal equivalents thereof.

What is claimed is:

1. An inspection device for nondestructive evaluation of an aircraft, comprising:

a cart;

a nondestructive testing device coupled the cart; and, a computer coupled to the cart and nondestructive testing device, the computer configured to:
  receive aircraft positional data from positional receivers mounted on an aircraft;
  overlay a model of the aircraft on the received aircraft positional data to determine a coordinate system for the aircraft; and
  determine the location of the cart from data received from onboard positional receivers, the location of the cart referenced to the coordinate system for the aircraft.

2. The device of claim 1 wherein the model of the aircraft is overlaid on the retrieved aircraft positional data by use of a best fit calculation.

3. The device of claim 2 wherein the model of the aircraft is derived from schematic drawings.

4. The device of claim 2 wherein a plurality of testing points are determined for the model of the aircraft.

5. The device of claim 4 wherein a test vector is calculated for each test
  point, the test vector indicating a position to place the nondestructive test device.

6. The device of claim 1 wherein the computer is further configured to
  retrieve the model of the aircraft from a memory.

7. The device of claim 1 wherein the computer is farther configured to
  display a representation of the aircraft to assist an operator in navigation.

8. The device of claim 7 wherein a representation of the inspection device is displayed by the computer.

9. A system for the nondestructive evaluation of aircraft comprising
  a plurality of positional transmitters forming a perimeter around a test airplane;
  an inspection station within the perimeter comprising:
    a moveable cart;
    a nondestructive testing device coupled the cart; and
    a computer coupled to the cart and nondestructive testing device,
  the computer configured to:
    receive aircraft positional data from positional receivers mounted on an aircraft;
    overlay a model of the aircraft on the received aircraft positional data to determine a coordinate system for the aircraft; and
    determine the location of the cart from data received from onboard positional receivers, the location of the cart referenced to the coordinate system for the aircraft.

10. The system of claim 9 wherein the model of the aircraft is overlaid on the retrieved aircraft positional data by use of a best fit calculation.

11. The system of claim 10 wherein the model of the aircraft is derived from CAD drawings.

12. The system of claim 10 wherein a plurality of test points are determined for the model of the aircraft.

13. The system of claim 12 wherein a test vector is calculated for each test point, the test vector indicates the position to place the nondestructive test device.

14. The system of claim 9 wherein the computer is further configured to
  retrieve the model of the aircraft from memory.

15. The system of claim 9 wherein the computer is further operable to display a representation of the aircraft to assist an operator in navigation.

16. The system of claim 15 wherein a representation of the inspection device is displayed by the computer.

* * * * *